(12) United States Patent
Schmidt

(10) Patent No.: US 8,456,521 B2
(45) Date of Patent: Jun. 4, 2013

(54) TRIANGULATION CAMERA DEVICE AND TRIANGULATION IMAGING METHOD

(75) Inventor: Volker Schmidt, Berlin (DE)

(73) Assignee: Berliner Glas KGaA Herbert Kubatz GmbH & Co., Berlin (DE)

( * ) Notice: Subject to any disclaimer, the term of this patent is extended or adjusted under 35 U.S.C. 154(b) by 685 days.

(21) Appl. No.: 12/637,269

(22) Filed: Dec. 14, 2009

(65) Prior Publication Data
US 2011/0141252 A1 Jun. 16, 2011

(51) Int. Cl.
*H04N 7/18* (2006.01)

(52) U.S. Cl.
USPC .......................................................... 348/61

(58) Field of Classification Search
USPC .......................................................... 348/61
See application file for complete search history.

(56) References Cited

U.S. PATENT DOCUMENTS

| | | | |
|---|---|---|---|
| 4,415,239 A | 11/1983 | Humphrey | |
| 4,575,805 A | 3/1986 | Moermann et al. | |
| 4,730,910 A | 3/1988 | Humphrey | |
| 6,885,464 B1 | 4/2005 | Pfeiffer et al. | |
| 2004/0156626 A1 | 8/2004 | Thoms | |
| 2006/0227435 A1* | 10/2006 | Mueller et al. | 359/754 |
| 2011/0141252 A1* | 6/2011 | Schmidt | 348/61 |
| 2011/0221879 A1* | 9/2011 | Schmidt | 348/77 |
| 2011/0242281 A1* | 10/2011 | Schmidt | 348/46 |

FOREIGN PATENT DOCUMENTS

| | | |
|---|---|---|
| DE | 3143137 C2 | 10/1985 |
| DE | 10316416 A1 | 10/2004 |
| EP | 0968687 B1 | 1/2000 |

OTHER PUBLICATIONS

Bernd Breuckmann, "Bildverarbeitung und optische Messtechnik in der industriellen Praxis", p. 124, Franzis-Verlag GmbH, Muenchen, Germany (1993).
Milton Laikin, "Lens Design", Chapter 1—"The Method of Lens Design", Laikin Optical Corporation (2001).

* cited by examiner

*Primary Examiner* — Jerry Dennison
(74) *Attorney, Agent, or Firm* — Caesar, Rivise, Bernstein, Cohen & Pokotilow, Ltd.

(57) ABSTRACT

A triangulation camera device includes a light source device being adapted for generating illumination light to be directed onto an object under investigation and including a light source with an optical pattern generator and a first aperture being arranged along a first optical axis, a detector device being adapted for sensing reflection light reflected by the object and including a detector camera and a second aperture being arranged along a second optical axis, and an imaging optic having imaging lenses being adapted for imaging the illumination light onto the object and for collecting the reflection light, said imaging optic having a third optical axis, wherein the first, second and third optical axes are arranged in parallel and displaced relative to each other and the first and second apertures are arranged with a telecentric configuration relative to the imaging optic such that the illumination light and the reflection light are capable of forming a parallel illumination light bundle and a parallel reflection light bundle, resp., on the object side of the imaging optic, said illumination light bundle and said reflection light bundle having a predetermined projection angle, and the imaging lenses are tilted relative to the third optical axis such that surface reflections of the imaging lenses are directed toward ranges outside the second aperture.

14 Claims, 2 Drawing Sheets

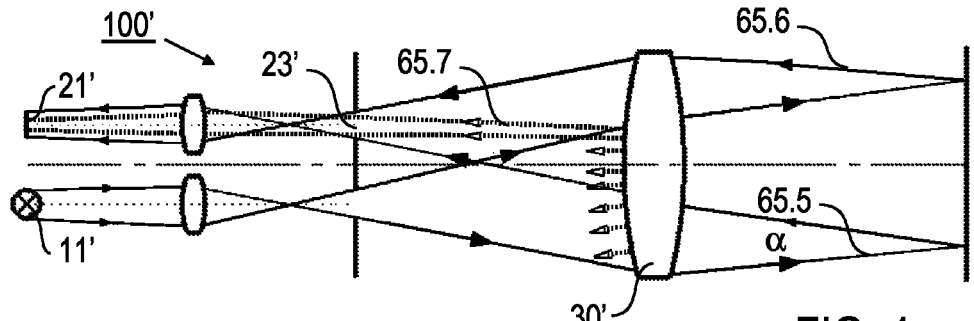
FIG. 4
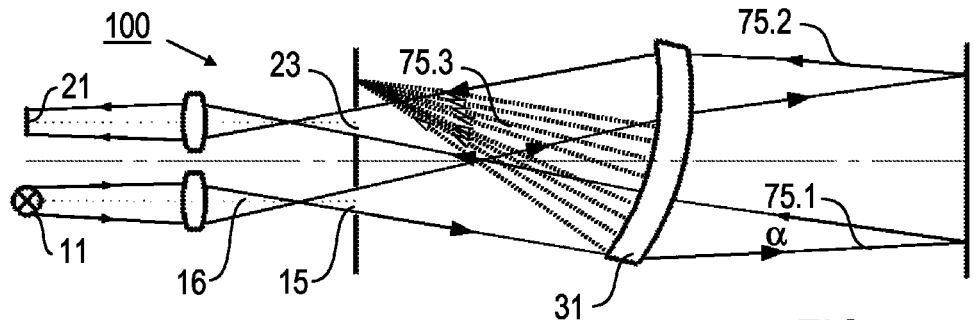
FIG. 5
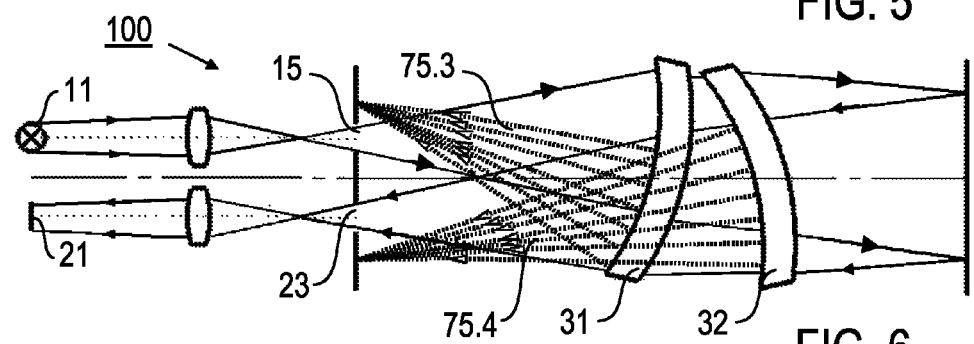
FIG. 6
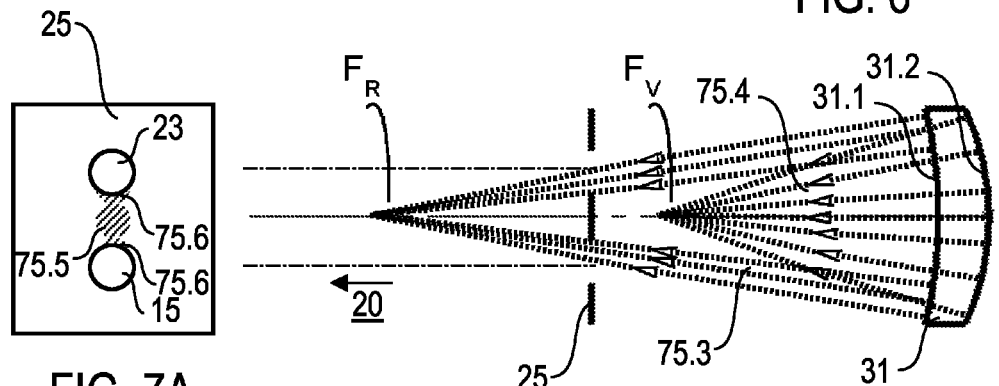
FIG. 7A
FIG. 7

TRIANGULATION CAMERA DEVICE AND TRIANGULATION IMAGING METHOD

TECHNICAL FIELD

The present invention relates to a triangulation camera device being in particular adapted for measuring of a surface of an object under investigation, like a medical object, e.g., a tooth or another part of a human body, or a workpiece. Furthermore, the present invention relates to a triangulation imaging method, in particular for investigating a surface of an object. Applications of the invention are present in medical imaging, in particular in intraoral dental imaging of a tooth surface, or in non-medical imaging, in particular in imaging of a workpiece surface.

TECHNICAL BACKGROUND

Triangulation cameras are adapted for illuminating an object and sensing reflection light reflected from the objects surface. The triangulation camera includes an imaging optic for imaging illumination light onto the object and for imaging reflection light reflected from the object on a detector camera. Triangulation cameras are simply used for obtaining an enlarged image of the objects surface or, with a more complex structure, for investigating (measuring) the shape of the objects surface with a pattern projection method (see textbook "Bildverarbeitung and optische Messtechnik in der industriellen Praxis" pp. 124, Bernd Breuckmann, 1993 Franzis-Verlag GmbH, Muenchen, Germany).

Most conventional triangulation cameras for small objects have a telecentric optical configuration providing a magnification being independent of an object distance of the camera. With small triangulation angles and low numerical apertures such systems allow single shot measurements of rather steep surfaces as e.g., a tooth which is prepared for insertion of an inlay. The telecentric optical configuration requires a complex imaging optic, which is constructed with multiple imaging lenses. The measurement field of such a telecentric triangulation measurement system is always lower than the size of the lens, which limits the application of telecentric triangulation systems to small objects.

The imaging optic can be simplified if a non-telecentric optical configuration is provided (see US 2004/0156626 A1). However, this results in a reduced imaging quality which may be unacceptable for precision applications of the triangulation camera. If the shape of the object's surface is to be reconstructed, e.g., for obtaining input data for prototyping a tooth filling, imaging precision down to a range of 5 µm to 10 µm is required.

For the simple monitoring purpose, the illumination light and the reflection light may travel with opposite directions along one common beam path. For the pattern projection method, the direction of illumination light must deviate from the direction of collecting the reflection light. In this case, additional requirements result for the optical set-up and in particular for the imaging optic as the illumination light and the reflection light do not travel along one beam path through the imaging optic. In particular, a telecentric optical configuration yielding oblique-angled beam paths is necessary, wherein optical axes of telecentric apertures are with displaced relative to the optical axis of the imaging optic.

The telecentric optical configuration, which is described with further details below, has an essential limitation in terms of the large light intensity loss at telecentric apertures. Therefore, imaging with conventional triangulation cameras can be deteriorated by scattering light, in particular by surface reflections at lens surfaces of the imaging optic.

Conventional approaches for suppressing surface reflections in standard cameras are based on anti-reflection coatings on lens surfaces or scatter light shielding apertures. It has been found in practice, that these techniques are not sufficient for triangulation cameras. Another conventional approach for suppressing surface reflections in special cameras or illumination devices is based on tilting lenses relative to the optical axis of the imaging optic. As an example, US 2006/0227,435 (or corresponding DE 103 164 16 A1) discloses an ophthalmologic camera for retina imaging having a main optic with pairwise tilted lenses. Further examples of using tilted lenses are described in U.S. Pat. No. 4,415,239 (or corresponding DE 31 43 137 C2) or U.S. Pat. No. 4,730,910 A. All the conventional techniques using tilted lenses for scatter reduction do not use telecentric optical configurations. Therefore, they cannot be used for triangulation measurement of steep surfaces as in dental cameras.

OBJECTIVE OF THE INVENTION

The objective of the invention is to provide an improved triangulation camera device, avoiding disadvantages of conventional techniques. In particular, the objective of the invention is to provide a triangulation camera device having an improved scatter light suppression and/or improved imaging properties. A further aspect of the objective of the invention is to provide an improved method of imaging a surface of small objects, like e.g., a tooth, avoiding disadvantages of conventional imaging methods.

The above objectives are achieved with methods or devices comprising the features of the invention.

SUMMARY OF THE INVENTION

According to a first general aspect of the invention, the above objective is solved by a triangulation camera device (or: measuring camera device) including an illumination device, an imaging optic and a detector device and having a telecentric configuration with oblique-angled beam paths of illumination and reflection light, wherein imaging lenses of the imaging optic are tilted relative to an optical axis of the imaging optic such that surface reflections of the imaging lenses are directed toward ranges outside a beam path to the detector device. Surface reflections comprise light, which has been reflected towards the detector device by the surfaces of the imaging lenses.

According to the invention, the triangulation camera includes a light source device which is arranged for generating illumination light to be directed onto an object under investigation. The light source device comprises a light source, e.g., an active monochromatic or polychromatic light source arranged in the triangulation camera or a passive light source, like an output of an optical fiber. The light source includes an optical pattern generator which is configured for creating the illumination light with a predetermined spatial modulation, i.e., an intensity pattern, like a stripe or grid pattern. The optical pattern generator may be attached to the light source or displaced therefrom. Furthermore, the light source device comprises a first aperture (illumination aperture) being arranged in a first optical axis of a beam path of the light source device (illumination beam path).

Furthermore, the inventive triangulation camera includes a detector device, which is arranged for sensing reflection light reflected by the small object. The detector device comprises a detector camera, e.g., a CCD camera, arranged in the triangulation camera or a passive image collector, like an input of a coherent optical fiber bundle. Furthermore, the detector device comprises a second aperture (detector aperture) being arranged in a second optical axis of a beam path of the detector device (reflection beam path).

The imaging optic of the inventive triangulation camera includes at least two imaging lenses defining a third optical axis of the imaging optic. For imaging the illumination light onto the small object and for collecting the reflection light from the small objects surface with the telecentric configuration with oblique-angled illumination and reflection beam paths, said first, second and third optical axes are arranged in parallel, but displaced relative to each other, and the first and second apertures are arranged in a focal plane of the imaging optic. On the object side of the imaging optic, the illumination light forms a parallel illumination light bundle and the reflection light forms a parallel reflection light bundle, said illumination light bundle and said reflection light bundle having a predetermined projection angle relative to each other.

According to the invention, the imaging lenses are tilted relative to the third optical axis such that surface reflections of the imaging lenses are directed toward ranges outside the second aperture. The inventor has found that the imaging lenses being designed for telecentric imaging of illumination and reflection light with oblique-angled beam paths can be tilted without a critical loss in imaging quality or light intensity. Furthermore, tilting of the imaging lenses allows a surface reflection suppression such that a single reflection image collected with the detector camera has sufficient quality for e.g., a surface analysis of e.g., a tooth with a steep hole. The inventive triangulation camera can be used in a single shot mode.

According to a second general aspect of the invention, the above objective is solved by an imaging method for investigating a surface of a small object, wherein a triangulation camera device according to the above first aspect of the invention is used. The inventive imaging method comprises a first step of illuminating the object surface with the spatially modulated illumination light. A light pattern is imaged (projected) onto the object surface. Due to the irregular topography of the object surface, the light pattern is deformed in a characteristic fashion. In a further step, a reflection image of reflection light reflected by the object surface is sensed using the imaging optic and the detector device. The reflection light is spatially modulated as well. However, the light pattern of the reflection image (reflection pattern) is changed compared with the illumination light pattern due to the deformation on the object surface and the projection angle of the illumination and reflection light bundles. Furthermore, the reflection light is free of surface reflections, in particular free of focused surface reflections created by the imaging lenses. Finally, the shape of the object surface is reconstructed by analyzing the reflection pattern. A reconstruction algorithm is used which is based on a conventional triangulation method, as described e.g., by "Bildverarbeitung and optische Messtechnik in der industriellen Praxis" pp. 124, Bernd Breuckmann, 1993 Franzis-Verlag GmbH, Muenchen, Germany).

The triangulation camera device may be configured as a medical camera for medical imaging, or as a test camera for non-medical imaging. According to the invention, the object under investigation may comprise a medical object under investigation, like a tooth, a hollow organ, a vessel or a tissue, or a workpiece, or a part thereof. From a practical point of view, as a diameter of the optical objective has the same dimension as the region to be imaged in telecentric imaging, objects are imaged which have a characteristic size (e.g., diameter of imaged surface region) below 10 cm, preferably below 8 cm, in particular below 5 cm or below 3 cm, like e.g., 1 cm or smaller. Larger objects can be imaged if multiple portions of the surface thereof are investigated in succession.

Tilting of the imaging lenses introduces aberrations which deform the illumination and reflections light, resp. For the reconstruction of the shape of the object surface, those aberrations could be uncritical as they could be numerically compensated with the reconstruction algorithm. In particular, the reflection image could be subjected to a calibration for compensating aberrations of the imaging optic. However, for providing a visual image of the object, the aberrations are to be avoided. Therefore, according to a preferred embodiment of the invention, the imaging lenses are mutually tilted relative to the third optical axis such that aberrations resulting from lens tilting are compensated. Even in this case, a calibration of the reflection image for compensating possibly remaining aberrations of the imaging optic can be provided. Preferably, if the imaging optic includes an even number of imaging lenses, the imaging lenses are tilted in a reciprocal fashion such that the aberrations are compensated pair-wise. With this embodiment, the design of the imaging optic is facilitated.

According to a further preferred embodiment of the invention, the imaging lenses have concave surfaces facing to the first and second apertures. On the opposite sides facing to the object under investigation, the imaging lenses have convex surfaces. The concave surfaces on the aperture side have advantages for focusing the surface reflections.

According to a further preferred embodiment of the invention, the imaging lenses are tilted such that a first reflection on an illumination side of the imaging optic is deflected towards the illumination beam path. To this end, a first lens (entrance lens) of the imaging lenses being arranged on the illumination side of the imaging optic is tilted relative to the third axis towards the first aperture. This embodiment advantageously results in an effective surface reflection suppression as the first reflection which is not subjected to back-reflections at inner surfaces of the imaging lens represents a main portion of surface reflections.

Advantageously, various design options are available for directing the surface reflections out of the reflection beam path of the detector device. According to a first variant (in the following: first embodiment of the invention), the imaging lenses are designed such that surface reflections thereof are focused onto an aperture plane which includes the second aperture (detector aperture). For providing the telecentric configuration, both first and second apertures are arranged in a common aperture plane perpendicular to the first to third optical axes. Accordingly, the surface reflections can be focused onto this common aperture plane. This first embodiment of the invention has advantages in terms of collecting the surface reflections in one or more locally restricted focal points which can be set adjacent to the second aperture.

According to a second variant (in the following: second embodiment of the invention), the imaging lenses are designed such that surface reflections thereof are focused onto planes deviating from the common aperture plane. In this case, unfocused light spots of the surface reflections are formed in the common aperture plane. This second embodiment of the invention has advantages in terms of designing the imaging optic. The number of boundary conditions is reduced so that the structure of the imaging optic can be facilitated and/or the magnification of the imaging optic can be increased.

With the second embodiment of the invention, light portions of the unfocused light spots can be transmitted through the second aperture. In this case, for avoiding distortions of the reflection image, the imaging optic and the second aperture are adjusted such that the transmitted light portions are below a predetermined intensity limit, e.g., below 5%, preferably below 1% of the intensity of the respective surface reflection. Alternatively or additionally, the imaging optic, the second aperture and the beam path towards the detector camera are adjusted such that light portions transmitted through the second aperture are focused outside the beam path towards the detector camera, e.g., onto a shielding screen within the detector device.

BRIEF DESCRIPTION OF THE DRAWINGS

Further details and advantages of the invention are described in the following with reference to the attached drawings, which show in:

FIG. 4: a schematic illustration of conventional telecentric optical imaging without surface reflection suppression;

FIGS. 5 and 6: schematic illustrations of embodiments of telecentric optical imaging with surface reflection suppression; and FIGS. 7 and 7A: schematic illustrations of a particularly preferred embodiment of telecentric optical imaging with surface reflection suppression.

EMBODIMENTS OF THE INVENTION

Embodiments of the invention are described in the following with particular reference to the telecentric configuration and the inventive surface reflection suppression. Known details of triangulation cameras and the use thereof, in particular the design of a camera casing, the selection of a light source and/or a detector camera, quantitative features, like the size and geometry of the illumination pattern or the magnification of the imaging optic, the coupling with a control device, the reconstruction of a shape of an object surface are not described here as they are known as such from prior art. Furthermore, particular reference is made to a triangulation camera device configured as a medical camera for medical imaging, in particular a dental camera for imaging a tooth surface. Again, reconstructing of a tooth surface shape and obtaining input data for prototyping a tooth filling are known as such from prior art. The invention is not restricted to the dental camera application, but rather can be implemented in an analogue way with another medical camera or a technical test camera for imaging a workpiece.

1. Structural Components of the Inventive Triangulation Camera

Figure 1:
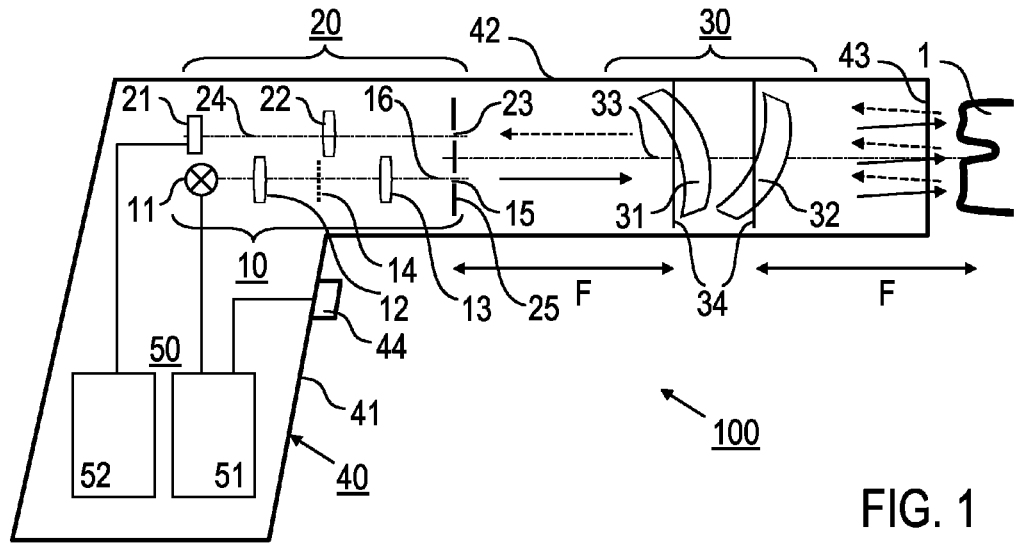
FIG. 1: a schematic illustration of a triangulation camera according to the invention.

Firstly, the structural components of the triangulation camera 100 are described. FIG. 1 schematically illustrates a sectional view of an inventive triangulation camera 100 comprising a light source device 10, a detector device 20 and an imaging optic 30, which are arranged in a casing 40. Optionally, the triangulation camera 100 may comprise a control device 50, which is accommodated in the casing 40 as well. The triangulation camera 100 is configured for imaging of a small object (e.g. a tooth) 1 under investigation.

The light source device 10 comprises a light source 11, like e.g., a laser diode or a light emitting diode, a combination of a collector lens 12 and a condenser lens 13, an optical pattern generator 14, like e.g., a transparent plate carrying am opaque strip or grid pattern, and a first aperture 15 (illumination aperture 15) centered on a first optical axis 16. The collector lens 12 and the condenser lens 13 are arranged for providing collimated illumination light (Koehler illumination). To this end, the light source 11 is arranged in the focal plane of the collector lens 12, while the optical pattern generator 14 is arranged in the focal planes of the collector and condenser lenses 12, 13, resp. The first aperture 15 is arranged in the focal plane of the condenser lens 13. The components 11 to 15 provide a part of an illumination beam path from the light source 11 to the object 1, wherein this part is extending along the first optical axis 16. Depending on the structure of the triangulation camera 100 and the available space in the casing 40, the illumination beam path may include further optical components, like lenses and/or deflection mirrors.

The detector device 20 comprises a detector camera 21, e.g., a CCD sensor, a collector lens 22 and a second aperture 23 (detector aperture 23) centered on a second optical axis 24. The collector lens 22 is adapted for forming a reflection image on the detector camera 21. To this end, the detector camera 21 and the second aperture 23 are arranged in the focal planes of the collector lens 22. The components 21 to 23 provide a part of a reflection beam path from the small object 1 to the detector camera 21, wherein this part is extending along the second optical axis 24. Again, depending on the camera structure and available space, the reflection beam path may include further optical components, like lenses, deflection mirrors and/or shielding screens.

The first and second apertures 15, 23 are arranged in a common aperture plane 25. In practice, the apertures 15, 23 each having a diameter of e.g., 1 mm to 2 mm are provided in a plane opaque sheet.

The imaging optic 30 has a third optical axis 33 on which two imaging lenses 31, 32 are arranged. The imaging optic 30 has two optical main planes 34 and a focal length F. For telecentric imaging the patterned illumination light onto the small object 1 and telecentric imaging the reflection light reflected by the small object 1, the imaging optic 30 is arranged such that the first and second apertures 15, 23 are arranged in an illumination side focal plane (common aperture plane 25) of the imaging optic 30, while the surface of the small object is arranged in an object side focal plane of the imaging optic 30. In other words, the distance of the common aperture plane 25 from the first optical main plane 34 is the focal length F of the imaging optic 30. Due to the telecentric configuration, adjusting the small object surface precisely in the object side focal plane is not strictly necessary.

The imaging lenses 31, 32 are tilted relative to the third optical axis 33. In other words, main planes of each of the imaging lenses are not perpendicular to the optical axis 33, or the symmetry axis of each of the imaging lenses deviates from the optical axis 33. The first imaging lens 31 having a concave shape is tilted towards the first aperture 15.

The imaging lenses 31, 32 are designed by selecting lens properties, in particular geometric parameters, like e.g., radius, thickness and/or curvature, material parameters, like e.g., the glass type, the refraction index and/or surface coatings, the mutual distances of the imaging lenses 31, 32, and the tilting angles of the imaging lenses 31, 32. Selecting the lens properties is conducted with available optimization algorithms (see e.g. "Lens Design" by Milton Laikin, Marcel Dekker, Inc. 2001) as it is known as such in the field of designing optical devices. For the optimization algorithm, optimization criteria of focusing the surface reflection in (or before/behind) the telecentric plane and compensating imaging aberrations, like e.g., coma, astigmatism, distortion, chromatic aberration, scattering and absorption, are applied.

The casing 40 is adapted for providing a handheld device with a hand piece 41 and a longitudinal tube piece 42 accommodating the optical components. The tube piece 42 has a window 43, through which illumination and reflection light is transmitted. Furthermore, a switch 44 may be provided for operating the control device 50. It is emphasized that the casing 40 is schematically illustrated. In practice, multiple variations can be provided, e.g., with regard to the position of window 43. If the window 43 opens in a radial direction relative to the third optical axis 33, a deflection mirror is arranged between the imaging optic 30 and the window.

The control device 50 comprises an illumination control circuit 51 and a detector control circuit 52. Both components may be implemented within a common circuit. The illumination control circuit 51 is configured for operating the light source 11, e.g., an operation time (exposure time) thereof. The detector control circuit 52 is configured for processing the reflection image obtained with the detector camera. With alternative embodiments, the control device 50 can be arranged outside the casing, e.g., in a base station (not shown).

For imaging the surface of a small object 1, spatially patterned illumination light is imaged with the imaging optic 30 onto the small object 1. A reflection image of reflection light with changed spatial pattern (reflection pattern) is imaged with the imaging optic 30 onto the detector camera 21. The shape of the object surface is reconstructed by analyzing the reflection pattern.

2. Optical Features of the Inventive Triangulation Camera

Figure 2:
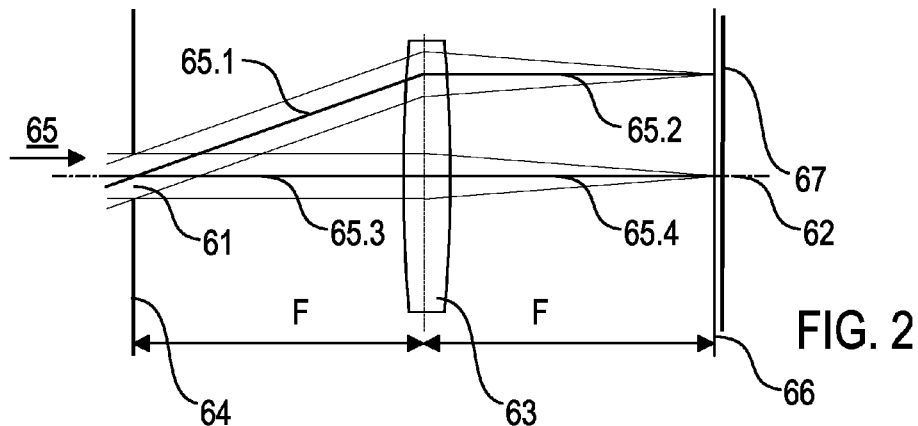
FIGS. 2 and 3: schematic illustrations of telecentric optical imaging (technical background)
Figure 3:
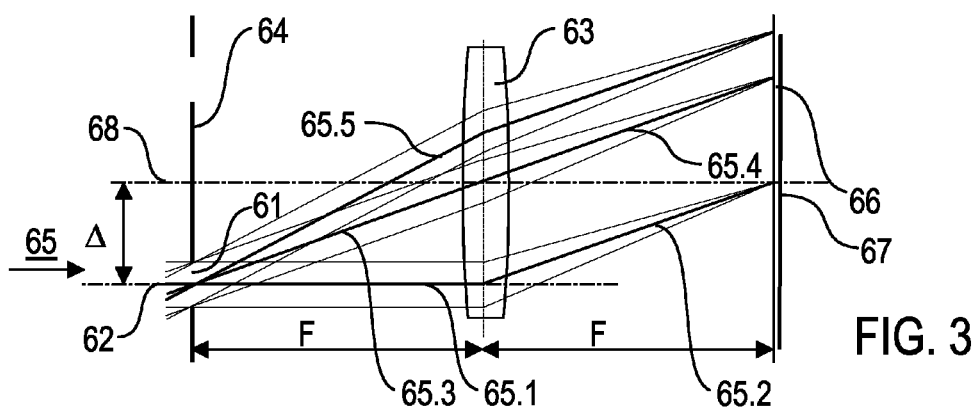

For explaining the optical features of the inventive triangulation camera, features of conventional telecentric optical imaging, in particular in a conventional triangulation camera 60 without surface reflection suppression are described at first (FIGS. 2 to 4). Subsequently, preferred features of the inventive triangulation camera are described (FIGS. 5 to 8). It is to be noted that for simplifying the illustration, reference is made to a single imaging lens in some cases. In practice, the single lens is replaced by a more complex lens arrangement of multiple imaging lenses.

Conventional Telecentric Set-Up

FIG. 2 shows the function of a telecentric aperture 61 arranged on an optical axis 62 at the focal distance F from an imaging lens 63, i.e., in the focal plane 64 of the imaging lens 63. Illumination light 65 is restricted by the telecentric aperture 61 so that only an inner cone-shaped part of the illumination light 65 near the optical axis 62 is transmitted to the imaging lens 63. According to the imaging properties of a lens, an oblique focal ray 65.1 is deflected towards a parallel ray 65.2, while a parallel ray 65.3 along the optical axis 62 is kept as a parallel ray 65.4. As a result, a bundle of parallel rays is directed toward an imaging plane 67 on an image-side of the imaging lens 63. If the imaging plane 67 coincidences with the focal plane 66 of the imaging lens 63, the parallel rays are focused. Due to the provision of a bundle of parallel rays, the magnification of the imaging lens 63 is independent of the distance of the imaging plane 67 from the imaging lens 63.

FIG. 3 (telecentric configuration with an oblique-angled beam path of illumination) shows the function of a telecentric aperture 61 arranged at the focal distance F in the focal plane 64 of the imaging lens 63. Contrary to FIG. 2, the telecentric aperture 61 is centered on an optical axis 68 displaced relative to the optical axis 62 of the imaging lens 63 by a distance Δ. With the restriction of the illumination light 65 by the telecentric aperture 61, a parallel ray 65.1 is deflected towards a oblique focal ray 65.2, while a centered ray 65.3 through the centre of the imaging lens 63 is kept as ray 65.4 without deflection. Any other ray 65.5 is deflected in parallel to ray 65.2, 65.4. Again, a bundle of parallel rays is directed toward the imaging plane 67 on the image-side of the imaging lens 63, so that the magnification of the imaging lens 63 is independent of the distance of the imaging plane 67 from the imaging lens 63.

In a triangulation camera, the telecentric configuration with an oblique-angled beam path is used for both of the illumination and reflection beam paths as illustrated in FIG. 4. On the object side of the imaging optic, a parallel illumination light bundle 65.5 and a parallel reflection light bundle 65.6 form a projection angle α. FIG. 4 shows the situation in a conventional triangulation camera 100' with a light source 11', a detector camera 21' and an imaging optic 30', wherein surface reflections 65.7 from the imaging optic 30' are directed through the reflection aperture 23' onto the detector camera 21'.

Telecentric Optical Imaging with Inventive Surface Reflection Suppression

FIG. 5 illustrates the optical components of an inventive triangulation camera 100 having a light source 11, a detector camera 21 and an imaging optic, which for clarity reasons are shown without the pattern generator and with a single imaging lens 31 only. Further components may be provided as described with reference to FIG. 1.

Patterned illumination light 75 traveling along the first optical axis 16 through the first aperture 15 is imaged by the imaging lens 31 as a bundle of deflected parallel rays 75.1 onto the object surface as shown in FIG. 3. After diffuse reflection on the object surface (schematically shown), a bundle of parallel reflected rays 75.2 having a projection angle α is collected by the imaging lens 31 and imaged through the second aperture to the detector camera 21.

Surface reflections 75.3 are formed at the glass surfaces of the imaging lens 31. Due to the tilting of the imaging lens, the surface reflections 75.3 can be directed into a range outside the second aperture 23. According to the first embodiment of the invention, in particular due to the concave shape, the surface reflections 75.3 can be focused effectively onto the aperture plane 25, so that a light spot formed by the surface reflections 75.3 is limited outside the second aperture 23.

Another example of the first embodiment of the invention is illustrated in FIG. 6, wherein the triangulation camera 100 has an imaging optic 30 with two imaging lenses 31, 32. The imaging lenses 31, 32 are alternately tilted such that surface reflections 75.3 from the first imaging lens 31 are focused above the first aperture 15, while surface reflections 75.4 from the second imaging lens 32 are focused below the second aperture 23. With the opposite tilting of both lenses, aberrations caused by the tilting are compensated at least partially.

FIG. 7 schematically illustrates the second embodiment of the invention wherein surface reflections are focused onto planes deviating from the common aperture plane 25. For illustrating the basic concept of the second embodiment, a non-tilted imaging lens is shown in FIG. 7. However, in practice tilted imaging lenses are used as shown in FIG. 6.

The focal length $F_R$ of the first concave surface 31.1 is larger than the focal length of the imaging lens 31. Accordingly, surface reflections 75.3 from the first concave surface 31.1 are focused in a plane behind the aperture plane 25. On the contrary, the focal length $F_V$ of the second concave surface 31.2 is shorter than the focal length of the imaging lens 31, so that surface reflections 75.4 from the second concave surface 31.2 are focused in a plane before the aperture plane 25. In both cases, surface reflections are directed into ranges outside of the detector beam path of the detector device 20. Furthermore, the surface reflections 75.3, 75.4 form unfocused spots 75.5, 75.6 on the aperture plane 25 (see FIG. 7A). Accordingly, the first surface reflections 75.3 are completely shielded in the aperture plane 25. The second surface reflections 75.4 are partially shielded only. Certain portions of the second surface reflections 75.4 are transmitted through the apertures 15 and 23. The imaging lens preferably is designed such that the transmitted light portions are less that 0.1% of the intensity of the surface reflection 75.4.

The features of the invention disclosed in the above description, the drawings and the claims can be of significance both individually as well as in combination for the realization of the invention in its various embodiments.

What is claimed is:

1. Triangulation camera device, comprising:
    a light source device being adapted for generating illumination light to be directed onto an object under investigation and including a light source with an optical pattern generator and a first aperture being arranged along a first optical axis, wherein the pattern generator is adapted for creating the illumination light with a predetermined spatial modulation,
    a detector device being adapted for sensing reflection light reflected by the object and including a detector camera and a second aperture being arranged along a second optical axis, and
    an imaging optic having imaging lenses being adapted for imaging the illumination light onto the object and for collecting the reflection light, said imaging optic having a third optical axis, wherein
    the first, second and third optical axes are arranged in parallel and displaced relative to each other and the first and second apertures are arranged with a telecentric configuration relative to the imaging optic such that the illumination light and the reflection light are capable of forming a parallel illumination light bundle and a parallel reflection light bundle, respectively, on an object side of the imaging optic, said illumination light bundle and said reflection light bundle having a predetermined projection angle, and
    the imaging lenses are tilted relative to the third optical axis such that surface reflections of the imaging lenses are directed toward ranges outside the second aperture.

2. Triangulation camera device according to claim 1, wherein the imaging lenses are tilted relative to the third optical axis such that lens tilting aberrations at the imaging lenses are compensated.

3. Triangulation camera device according to claim 1, wherein the imaging lenses have concave surfaces facing to the first and second apertures.

4. Triangulation camera device according to claim 1, wherein a first lens of the imaging lenses is arranged on a light source and detector side of the imaging optic, and is tilted towards the first aperture.

5. Triangulation camera device according to claim 1, wherein the imaging optic is designed such that the surface reflections are focused onto a common aperture plane including the first and second apertures.

6. Triangulation camera device according to claim 1, wherein the imaging optic is designed such that the surface reflections are focused onto planes deviating from a common aperture plane including the first and second apertures so that unfocused light spots of the surface reflections are formed in the aperture plane.

7. Triangulation camera device according to claim 6, wherein the imaging optic and the first and second apertures are designed such that light portions of the light spots transmitted through the second aperture are below a predetermined intensity limit.

8. Triangulation camera device according to claim 6, wherein the imaging optic and the first and second apertures are designed such that light portions of the light spots transmitted through the second aperture are focused outside a beam path of the reflection light in the detector device.

9. Triangulation camera device according to claim 1, wherein the imaging optic includes an even number of imaging lenses and the imaging lenses are tilted such that the aberrations are compensated pair-wise.

10. Triangulation camera device according to claim 1, which is configured as a medical camera for medical imaging or a test camera for non-medical imaging.

11. Imaging method for investigating a surface of an object, using a triangulation camera device according to claim 1, comprising the steps of:
    illuminating the object surface with the illumination light generated with an illumination pattern using the light source device and the imaging optic,
    sensing a reflection image of reflection light reflected by the object surface using the imaging optic and the detector device, wherein the reflection image has a reflection pattern depending on the illumination pattern and a shape of the object surface and the reflection image is free of surface reflections from the imaging optic, and
    reconstructing the shape of the object surface by analyzing the reflection pattern.

12. Imaging method according to claim 11, further comprising the step of subjecting the reflection image to a calibration for compensating aberrations of the imaging optic.

13. Imaging method according to claim 10, wherein the object comprises
    a medical object under investigation or a part thereof, or
    a workpiece or a part thereof.

14. Imaging method according to claim 13, wherein the medical object comprises a tooth, a hollow organ, a vessel, or a tissue.

* * * * *